(12) United States Patent
Rusek et al.

(10) Patent No.: US 8,556,999 B2
(45) Date of Patent: Oct. 15, 2013

(54) RENEWABLE ENGINE FUEL AND METHOD OF PRODUCING SAME

(75) Inventors: John J Rusek, West Lafayette, IN (US); Mary-Louise Rusek, West Lafayette, IN (US); Jonathon D Ziulkowski, West Lafayette, IN (US); Justin D Zink, West Lafayette, IN (US)

(73) Assignee: Swift Fuels, LLC, West Lafayette, IN (US)

( * ) Notice: Subject to any disclaimer, the term of this patent is extended or adjusted under 35 U.S.C. 154(b) by 499 days.

(21) Appl. No.: 12/717,480

(22) Filed: Mar. 4, 2010

(65) Prior Publication Data

US 2010/0268005 A1    Oct. 21, 2010

Related U.S. Application Data

(63) Continuation-in-part of application No. 12/139,428, filed on Jun. 13, 2008, now Pat. No. 8,049,048, which is a continuation-in-part of application No. 11/881,565, filed on Jul. 27, 2007, now abandoned.

(51) Int. Cl.
*C10L 1/10* (2006.01)

(52) U.S. Cl.
USPC ............ 44/307; 44/605; 435/148; 435/160; 585/240; 585/319; 585/331; 585/409

(58) Field of Classification Search
USPC ............ 44/307, 605; 435/148, 160; 585/240, 585/319, 331, 357, 409
See application file for complete search history.

(56) References Cited

U.S. PATENT DOCUMENTS

| 1,315,585 A | 9/1919 | Weizmann |
| 1,713,589 A | 5/1929 | Bereslavsky |

(Continued)

FOREIGN PATENT DOCUMENTS

| EP | 0460957 | 12/1991 |
| EP | 0526129 | 2/1993 |

(Continued)

OTHER PUBLICATIONS

Abstract of Zaldivar, J. et al., Appl. Microbiol. Biotechnol. (2001) pp. 17-34, vol. 56.

(Continued)

*Primary Examiner* — Cephia D Toomer
(74) *Attorney, Agent, or Firm* — Woodard, Emhardt, Moriarty, McNett & Henry LLP

(57) ABSTRACT

The present invention provides non-petroleum high-octane fuel derived from biomass sources, and a method of producing same. The method of production involves reducing the biomass feedstocks to sugars, fermenting the sugars using microorganisms or mutagens thereof to produce ethanol or acetic acid, converting the acetic acid or ethanol to acetone, and converting the acetone to mesitylene and isopentane, the major components of the renewable engine fuel. Trimerization of acetone can be carried out in the presence of a catalyst containing at least one metal selected from the group consisting of niobium, iron and manganese. The ethanol can be converted to mesitylene in a dehydration reaction in the presence of a catalyst of zinc oxide/calcium oxide, and unreacted ethanol and water separated from mesitylene by distillation. These ethanol-based, biomass-derived fuels are fully renewable, may be formulated to have a wide range of octane values and energy, and may effectively be used to replace 100 LL aviation fuel (known as AvGas), as well as high-octane, rocket, diesel, turbine engine fuels, as well as two-cycle, spark-ignited engine fuels.

16 Claims, 8 Drawing Sheets

(56) References Cited

U.S. PATENT DOCUMENTS

| | | |
|---|---|---|
| 2,401,983 A | 6/1946 | Stanly et al. |
| 2,413,262 A | 12/1946 | Stirton |
| 2,422,674 A | 6/1947 | Haensel et al. |
| 2,425,096 A | 8/1947 | Ipatieff et al. |
| 2,506,539 A | 5/1950 | Boardman |
| 2,593,561 A | 4/1952 | Herbst et al. |
| 2,917,561 A | 12/1959 | Eby |
| 3,201,485 A | 8/1965 | Kovach |
| 3,267,165 A | 8/1966 | Kimble et al. |
| 3,301,912 A | 1/1967 | Hwang et al. |
| 3,946,079 A | 3/1976 | Mizutani et al. |
| 4,006,149 A | 2/1977 | Bonnemann et al. |
| 4,300,009 A * | 11/1981 | Haag et al. ............ 585/408 |
| 4,368,056 A * | 1/1983 | Pierce et al. ............ 44/389 |
| 4,398,920 A * | 8/1983 | Guibet et al. ............ 44/438 |
| 4,398,921 A | 8/1983 | Rifkin et al. |
| 5,063,156 A | 11/1991 | Glassner et al. |
| 5,087,781 A | 2/1992 | Schutz et al. |
| 6,271,433 B1 | 8/2001 | Keady et al. |
| 6,353,143 B1 | 3/2002 | Fang et al. |
| 6,555,350 B2 | 4/2003 | Ahring et al. |
| 6,648,930 B2 | 11/2003 | Ulrich et al. |
| 6,908,591 B2 | 6/2005 | MacPhee et al. |
| 6,982,155 B1 | 1/2006 | Fukuda et al. |
| 6,991,810 B1 | 1/2006 | Grundy et al. |
| 6,998,050 B2 | 2/2006 | Nakajoh et al. |
| 7,141,083 B2 | 11/2006 | Jordan |
| 7,462,207 B2 | 12/2008 | Clark |
| 7,834,230 B2 | 11/2010 | Fujimoto et al. |
| 2002/0055663 A1 | 5/2002 | Barnes et al. |
| 2003/0183554 A1 | 10/2003 | Bazzani et al. |
| 2004/0020106 A1 | 2/2004 | Tack et al. |
| 2006/0051848 A1 | 3/2006 | Nishio et al. |
| 2007/0135318 A1 | 6/2007 | Singh et al. |
| 2007/0175088 A1 | 8/2007 | Selkirk |
| 2008/0168706 A1 | 7/2008 | Rusek et al. |
| 2008/0244961 A1 | 10/2008 | Rusek et al. |
| 2008/0244962 A1 | 10/2008 | Abhari et al. |
| 2009/0000185 A1 | 1/2009 | Aulich et al. |
| 2009/0013591 A1 | 1/2009 | Braden et al. |
| 2009/0117619 A1 | 5/2009 | Hutcheson et al. |
| 2009/0203098 A1 | 8/2009 | Verser |
| 2010/0268005 A1 | 10/2010 | Rusek et al. |
| 2010/0298615 A1 | 11/2010 | Rusek et al. |

FOREIGN PATENT DOCUMENTS

| | | |
|---|---|---|
| JP | 57145181 | 9/1982 |
| JP | 62-278989 | 12/1987 |
| WO | WO 98/51813 | 11/1998 |
| WO | WO 2008/013922 A1 | 1/2008 |
| WO | 2009152495 A2 | 12/2009 |

OTHER PUBLICATIONS

International Search Report issued on Nov. 8, 2011 in corresponding International Application No. PCT/US2011/026948.
Bird, C.W., Transition Metal Intermediates in Organic Syntehsis, New York, Lond: Academic Press, 1967, pp. 1-29.
Colket et al., Development of an Experimental Database and Kinetic Models for Surrogate Jet Fuels, Mar. 1, 2007, American Institute of Aeronautics, pp. 1-21.
International Search Report and Written Opinion issued on Oct. 19, 2011, in corresponding International Application No. PCT/US2011/037505.
Roubaud et al, Oxidation and Combustion of Low Alkylbenzenes at High Pressure, 2000, Combustion and Flame 121:535-541.

\* cited by examiner

RENEWABLE ENGINE FUEL AND METHOD OF PRODUCING SAME

REFERENCE TO RELATED APPLICATIONS

This is a continuation-in-part of International Application No. PCT/US 2009/047344, filed Jun. 15, 2009, which is an International Application of U.S. patent application Ser. No. 12/139,428, filed Jun. 13, 2008, now pending, itself a continuation-in-part of 11/881,565, filed Jul. 7, 2007, now pending, the contents of all of which are incorporated herein by reference.

FIELD OF THE INVENTION

The present invention relates in general to an engine fuel produced from renewable materials and, in particular, a non-petroleum fuel produced from renewable biomass materials. Several methods of producing same utilizing various biomass feedstocks is provided, in which bioderived feedstocks are reduced to sugars, the sugars are converted to ethanol or acetic acid, the acetic acid or ethanol is converted to acetone, and the acetone converted to mesitylene and other hydrocarbons such as isopentane, the major components of the renewable engine fuel. Further, biomass may be converted directly to acetone via a conventional or modified ABE process. The fuel may be formulated with a variety of octane ratings, depending on application within a high-octane reciprocating spark ignited engine, as well as two-cycle, spark-ignited engines. Further, the components of the renewable fuel can be mixed to form jet turbine fuel and diesel fuel.

BACKGROUND OF THE INVENTION

With the end of cheap oil and the mounting peak of world oil production, it is recognized that petroleum is a non-renewable resource, and will eventually be depleted. This realization has sparked a renewed interest in the development of renewable sources for fuel. This is particularly true in the case of aviation fuels used in internal combustion engines, as well as for jet (aviation) fuels.

Ethanol-based fuels for internal combustion engines have been available for roughly five decades. The State of California originated mandatory oxygenation of motor fuels, which includes ethanol-based fuels, partly to decrease the wholesale cost of fuel, and to a lesser extent to reduce air pollution per gallon of gasoline consumed. A key benefit of ethanol-based fuels is that they have a slightly higher pump octane number than ethanol-free gasoline. This is the reason many oil companies provide high ethanol content premium fuels, and lower ethanol content regular grades of gasoline. However, since ethanol-based fuels have lower energy, pollution is generally effectively increased per mile. To address this issue, research into renewable fuels made from some chemical species other than ethanol has been conducted, and such fuels have been found to exhibit significantly higher octane numbers and increased energy per unit volume when compared to commercial fuels and ethanol-based fuels.

Octane (Power)

Octane number is a measure of the effectiveness of power production. It is a kinetic parameter, therefore difficult to predict. Oil companies compiled volumes of experimental octane data (for most hydrocarbons) for the Department of Defense in the 1950's. For example, 2,2,4-trimethyl pentane (isooctane) has a defined octane number of 100, and n-heptane has a defined octane number of 0, based on experimental tests. Octane numbers are linearly interpolated and are generally hard to extrapolate, hence some predictions for mixes can be made only once pure sample values are determined.

Automobile gasoline is placarded at the pump as the average of research and motor octane numbers. These average octane numbers correlate to running a laboratory test engine (CFR) under less severe and more severe conditions, respectively, and calculating the average octane exhibited under these conditions. True octane numbers lie between the research and motor octane values. Aviation fuel has a "hard" requirement of 100 motor octane number (MON); ethanol has a MON of 96, which makes its use viable only when mixed with other higher octane components that are capable of increasing the MON to at least 100. Conventional 100 octane low lead (100 LL) contains about 3 ml of tetraethyl lead per gallon.

Range (Energy)

The inherent energy contained within gasoline is directly related to mileage, not to octane number. Automobile gasoline has no energy specification, hence no mileage specification. In contrast, aviation fuels, a common example being 100 LL, have an energy content specification. This translates to aircraft range and to specific fuel consumption. In the octane examples above, i-octane and n-heptane had values of 100 and 0, respectively. From an energy perspective, they contain heat of combustion values of 7.84 and 7.86 kcal/ml, respectively, which is the reverse of what would be expected based on power developed. Aircraft cannot compromise range due to the sensitivity of their missions. For this reason, energy content is equally important as MON values.

The current production volume of 100 LL is approximately 850,000 gallons per day. 100 LL has been designated by the Environmental Protection Agency (EPA) as the last fuel in the United States to contain tetraethyl lead. This exemption will likely come to an end in the future. In the United States, the Federal Aviation Administration (FAA) is responsible for setting the technical standards for aviation fuels. Currently, the FAA uses ASTM D910 as one of the important standards for aviation fuel. In particular, this standard defines 100 LL aviation gasoline. Thus any replacement 100 LL will likely also need to meet ASTM D910.

Although a number of chemical compounds have been found to satisfy the motor octane number for 100 LL octane aviation fuel, they fail to meet a number of other technical requirements for aviation fuel. This is true, for example, for isopentane, 90 MON, and sym-trimethyl benzene 136 MON. Pure isopentane fails to qualify as an aviation fuel because it does not pass the ASTM specification D909 for supercharge octane number, ASTM specification D2700 for motor octane number, and ASTM specification D5191 for vapor pressure.

Pure sym-trimethyl benzene (mesitylene) also fails to qualify as an aviation fuel because it does not pass ASTM specification D2386 for freeze point, ASTM specification D5191 for vapor pressure, and ASTM specification D86 for the 10% distillation point. Table 3 herein shows these test results and the ASTM standard for both isopentane and sym-trimethyl benzene.

The fermentation of a biomass using microbes to produce acetone and butanol was first discovered by Chaim Weizmann in 1916 and is described in U.S. Pat. No. 1,315,585 and other corresponding patents throughout the world. This process, known as the Weizmann process, was used by both Great Britain and the United States in World Wars I and II to produce acetone for the production of cordite used in making smokeless powder, and also for the derived butyrate dopes, used in aircraft surface covering.

A method has been discovered for producing ethanol from a plant material by (a) providing saccharophagus degradans strain 2-40, (b) growing the saccharophagus degradans strain 2-40 in a first portion of the plant material, and (c) harvesting protein from saccharophagus degradans strain 2-40, and mixing the protein with a second portion of the plant material and yeast in an aqueous mixture. This process is described in U.S. Patent Application Publication No. US 2009/0117619 A1 (May 7, 2009), the contents of which are incorporated herein by reference.

A number of methods are known for making mesitylene from acetone and include, for example:

liquid phase condensation of acetone in the presence of strong acids, e.g. sulfuric acid and phosphoric acid, as described in U.S. Pat. No. 3,267,165 (1966);

vapor phase condensation of acetone in the presence of a tantalum containing catalysts, as described in U.S. Pat. No. 2,917,561 (1959);

vapor phase condensation of acetone in the presence of a catalyst employing phosphates of the metals of group IV of the periodic system of elements, e.g. titanium, zirconium, hafnium and tin as described in U.S. Pat. No. 3,94,079 (1976);

vapor phase reaction of acetone in the presence of molecular hydrogen and a catalyst selected from alumina containing chromia and boria as described in U.S. Pat. No. 3,201,485 (1965);

vapor phase reaction of acetone using catalysts containing molybdenum as described in U.S. Pat. No. 3,301,912 (1967) or tungsten as described in U.S. Pat. No. 2,425,096; a vapor phase reaction of acetone over a niobium supported catalyst with high selectivity. The catalyst is preferably made by impregnating a silica support with an ethanolic solution of $NbCl_5$ or an aqueous solution of a niobium compound in order to deposit 2% Nb by weight and by calcining the final solid at 550° C. for 18 hours at 300° C. The condensation of acetone produces mainly mesitylene (70% selectivity) at high conversion (60-80% wt) as described in U.S. Pat. No. 5,087,781.

It is known that alkynes can be cyclotrimerized over transition metal catalysts to form benzene derivatives (C. W. Bird in "Transition Metal Intermediates in Organic Synthesis", New York, London: Academic Press, 1967, pp. 1-29) and U.S. Pat. No. 4,006,149). It is also known in the art to dimerize acetone to form isopentane. This process involves first dimerizing acetone to form diacetone alcohol which is then dehydrated to form mesitytl oxide. The mesityl oxide then undergoes gas phase reformation hydrogenation to form isopentane.

Although the prior art describes various methods in which acetone can be trimerized to form mesitylene in acid media, as well as various gas phase reactions in which acetone is trimerized in acidic heterogeneous catalytic surfaces such as silica gel, there still exists the problem of controlling the (1) extent of reaction (dimerization as opposed to trimerization) as well as (2) the selectivity of the reaction (minimization of unreacted side products) while maintaining (3) high throughput.

Accordingly, an object of the present invention is to obtain a catalyst in which the extent of dimerization and trimerization can be controlled with minimization of side reactions while maintaining a high throughput.

However, there are no known prior art processes capable of producing an engine fuel directly from biomass feedstock that satisfies FAA requirements. Furthermore, there are no known prior an processes involving the use of bacterial-based fermentation of a biomass to produce acetone, and then using gas phase reactions at elevated temperatures to form mesitylene and isopentane from the acetone.

Accordingly, it is an object of the present invention to provide a biomass-derived lead free renewable fuels that effectively replaces high-octane gasoline.

It is another object of the present invention to provide fully renewable fuels for aircraft which replaces 100 LL aviation gasoline. It is a further object of the present invention to provide high energy renewable fuels for use in turbines and other heat engines by the same methodology; the energy content and physical properties of the renewable components being tailored to the type of engine to be fueled.

It is another object of the present invention to provide a binary mixture of components which meet the technical specifications for aviation fuel of 100 LL octane. It is another object of the present invention to provide a non-petroleum based aviation fuel as a replacement of 100 LL octane which meets the technical specifications of the Federal Aviation Administration for 100 LL octane petroleum-based aviation fuels. It is still another object of the present invention to provide a process for the production of a biomass-derived fuel using bacteriological fermentation to produce of the components of a binary chemical mixture which satisfies the technical specifications for 100 LL octane aviation fuel. It is yet another object of the present invention to provide a process for the production of a new chemical-based 100 LL octane aviation fuel from renewable sources.

SUMMARY OF THE INVENTION

In order to achieve the objects of the present invention, the present inventors have arduously conducted research to develop a fully renewable engine fuel derived from various biomass feedstocks which has a high-octane rating and high energy content. Further, the present inventors have performed extensive research in order to identify viable processes for efficiently converting biomass-derived sugars to ethanol or acetic acid to acetone via a bacterium fermentation process, then converting the ethanol to mesitylene in a dehydration reaction, or converting the resulting acetic acid to acetone if need be, and then converting the acetone to mesitylene and isopentane, the basic components of the renewable fuel.

In a first preferred embodiment, a method is provided for producing bio-mass derived high-octane fuel, comprising the steps of:

(a) fermenting a biomass with a microorganism or a mutagen thereof to produce a mixture of metabolites comprising acetone and butanol;

(b) separating the acetone from butanol and any ethanol or other solvents in the mixture by fractional distillation;

(c) dimerizing a portion of resultant acetone from step (b) to form isopentane;

(d) trimerizing another portion of the acetone from step (b) using a catalyst containing at least one metal selected from the group consisting of niobium, iron, and manganese to form mesitylene, and (e) mixing the mesitylene with the isopentane from steps (c) and (d), whereby to form the biomass-derived high-octane fuel.

In a second preferred embodiment, there is provided in the first preferred embodiment a method of producing bio-mass derived high-octane fuel, wherein the microorganisms are one or more chosen from among moorella thermoaceticum, thermoanaerobacter kiwi, moorella thermoacetica, moorella thermoautotrophica, moorella thermoaeticum, moorella thermoautotrophicum, thermoanaerobacter thermosaccharolyticum, moorella thermoaceticum, and saccharophagus degradans, strain 2-40.

In a third preferred embodiment, there is provided in the first preferred embodiment a method of producing bio-mass derived high-octane fuel, wherein the biomass is selected from the group consisting of sugars, celluloses, lignins, starches, and lignocelluloses.

In a fourth preferred embodiment, there is provided in the first preferred embodiment a method of producing bio-mass derived high-octane fuel, wherein the biomass is selected from the group consisting of hard woods, grasses, corn stover, sorghum, corn fiber, and oat hulls, which are pretreated with enzymes or strong acids to break any hemicellulose chains into their sugar monomers.

In a fifth preferred embodiment, there is provided in the first preferred embodiment a method of producing bio-mass derived high-octane fuel, wherein the fermentation in step (a) is conducted in an anaerobic reactor in the absence of oxygen.

In a sixth preferred embodiment, there is provided in the first preferred embodiment a method of producing bio-mass derived high-octane fuel, wherein metabolites of acetone, butanol and ethanol from step (a) are stripped from the mixture produced in the fermentation process in step (a) when concentrations thereof over 2 to 3 wt % are obtained, whereby to avoid any poisoning of the microorganism.

In a seventh preferred embodiment, there is provided in the first preferred embodiment a method of producing bio-mass derived high-octane fuel, wherein the trimerizing of acetone in step (d) is carried out in the gas phase by passing acetone in contact with a catalyst containing niobium oxide at elevated temperatures. Preferably, this process is conducted within a temperature range of 200-600° C.

In an eighth preferred embodiment, there is provided in the first preferred embodiment a method of producing bio-mass derived high-octane fuel, wherein the dimerization of acetone in step (c) is carried out in a catalytic reaction to yield isopentane.

In a ninth preferred embodiment, there is provided in the first preferred embodiment a method of producing bio-mass derived high-octane fuel, wherein the dimerization of acetone in step (c) is carried out in a gas phase catalytic reaction.

In a tenth preferred embodiment, there is provided in the seventh preferred embodiment above a method of producing bio-mass derived high-octane fuel, wherein the trimerization of acetone in step (d) is carried out with a catalyst of niobium oxide on a base of alumina washcoat on calcined aluminized stainless steel corrugated film.

In an eleventh preferred embodiment, there is provided in the seventh preferred embodiment above a method of producing biomass derived high-octane fuel, wherein the trimerization of acetone in step (d) is carried out with a catalyst of niobium oxide on a base of alumina beads.

In a twelfth preferred embodiment, there is provided in the seventh preferred embodiment above a method of producing biomass derived high-octane fuel, wherein the trimerization of acetone in step (d) is carried out with a catalyst of niobium oxide on silica gel.

In a thirteenth preferred embodiment, there is provided in the seventh preferred embodiment above a method of producing biomass derived high-octane fuel, wherein the trimerization of acetone in step (d) is carried out with a catalyst of manganese nitrate on alumina beads.

In a fourteenth preferred embodiment, there is provided in a seventh preferred embodiment above a method of producing biomass derived high-octane fuel, wherein the trimerization of acetone in step (d) is carried out with a catalyst of manganese nitrate on silica gel.

In a fifteenth preferred embodiment, there is provided in the seventh preferred embodiment above a method of producing biomass derived high-octane fuel, wherein the trimerization of acetone in step (d) is carried out with a catalyst of manganese nitrate on a base of alumina washcoat on calcined aluminized stainless steel corrugated film.

In a sixteenth preferred embodiment, there is provided a method of producing biomass derived high-octane fuel, comprising the steps of:

(a) fermenting a biomass with a microorganism or a mutagen thereof to produce a mixture of metabolites comprising ethanol;

(b) carrying out a dehydration reaction of ethanol in the presence of a zinc oxide catalyst on a calcium base at elevated temperatures of about 350° C. and at elevated pressures; and (c) cooling vapors from the dehydration reaction to condense water and separate unreacted ethanol to acetone through distillation to form the resultant mesitylene.

In a seventeenth preferred embodiment, there is provided in the sixteenth preferred embodiment above a method of producing biomass derived high-octane fuel, wherein the microorganisms are one or more chosen from among moorella thermoaceticum, thermoanacrobacter kivui, moorella thermoacetica, moorella thermoautotrophica, moorella thermoacticum, moorella thermoautotrophicum, thermoanaerobacter thermosaccharolyticum, moorella thermoaceticum, and saccharophagus degradans, strain 2-40.

In an eighteenth preferred embodiment, there is provided in the sixteenth preferred embodiment above a method of producing biomass derived high-octane fuel, wherein the biomass is selected from the group consisting of sugars, celluloses, lignins, starches, and lignocelluloses.

In a nineteenth preferred embodiment, there is provided in the sixteenth preferred embodiment a method of producing biomass derived high-octane fuel, wherein ethanol is produced from a plant material comprising the steps of:

(a) providing saccharophagus degradans, strain 2-40;

(b) growing the saccharophagus degradans, strain 2-40 in a first portion of the plant material;

(c) harvesting protein from saccharophagus degradans, strain 2-40, and (d) mixing the protein with a second portion of the plant material and yeast in an aqueous mixture, thereby producing ethanol.

In a twentieth preferred embodiment, there is provided in the nineteenth preferred embodiment above a method of producing biomass derived high-octane fuel, wherein the aqueous mixture contains from about 1% to about 10% salt.

In a twenty first preferred embodiment, a method of producing biomass derived high-octane fuel is provided, comprising the steps of:

(a) growing saccharophagus degradans, strain 2-40, in a first portion of plant material;

(c) harvesting protein from saccharophagus degradans, strain 2-40 from the first portion of plant material;

(d) mixing the protein with a second portion of the plant material and yeast in an aqueous mixture, thereby producing ethanol;

(e) converting the ethanol in whole or in part to acetone;

(f) separating the acetone from any remaining ethanol and/or other byproducts;

(g) dimerizing a portion of the acetone from step (f) to form isopentane;

(h) trimerizing another portion of the acetone from step (f) using a catalyst containing at least one metal and/or oxide thereof selected from the group consisting of niobium, iron, and manganese to form mesitylene, and (i) mixing the mesitylene with the isopentane from steps (c) and (d), whereby to form the biomass-derived high-octane fuel.

In a twenty second preferred embodiment, the method of producing biomass derived high-octane fuel of the twenty first embodiment above is provided, wherein the ethanol is converted to acetone in the presence of iron oxide catalysts.

In a twenty third preferred embodiment, the method of producing biomass derived high-octane fuel of the twenty first embodiment above is provided, wherein the ethanol is converted to acetone in the presence of zinc oxide-calcium oxide catalysts and water vapor.

In a twenty-fourth preferred embodiment there is provided in the twenty-first embodiment a method of producing biomass derived high-octane fuel, wherein the ethanol is converted to acetone by a gas phase catalystic reaction at elevated temperatures.

In a twenty-fifth preferred embodiment there is provided in the twenty-first embodiment a method of producing bio-mass derived high-octane fuel, wherein the trimerizing of acetone in step (h) is carried out in the gas phase by passing acetone in contact with a catalyst containing niobium oxide at elevated temperatures.

In a twenty-sixth preferred embodiment there is provided in the twenty-first preferred embodiment a method of producing bio-mass derived high-octane fuel, wherein the dimerization of acetone in step (g) is carried out in a catalytic reaction to yield isopentane.

In a twenty-seventh preferred embodiment there is preferred in the twenty-first preferred embodiment a method of producing bio-mass derived high-octane fuel, wherein the dimerization of acetone in step (g) is carried out in a gas phase catalytic reaction.

In a twenty-eighth preferred embodiment there is provided in the twenty-first preferred embodiment a method of producing bio-mass derived high-octane fuel, wherein the trimerization of acetone in step (g) is carried out with a catalyst of niobium oxide on a base of alumina washcoat on calcined aluminized stainless steel corrugated film.

In a twenty-ninth preferred embodiment there is provided in the twenty-first preferred embodiment a method of producing biomass derived high-octane fuel, wherein the trimerization of acetone in step (g) is carried out with a catalyst of niobium oxide on a base of alumina beads.

In a thirtieth preferred embodiment there is provided in the twenty-first preferred embodiment a method of producing biomass derived high-octane fuel, wherein the trimerization of acetone in step (g) is carried out with a catalyst of niobium oxide on silica gel.

In a thirty-first preferred embodiment there is provided in the twenty-first preferred embodiment a method of producing biomass derived high-octane fuel, wherein the trimerization of acetone in step (g) is carried out with a catalyst of manganese nitrate on alumina beads.

In a thirty-second preferred embodiment there is provided in the twenty-first preferred embodiment a method of producing biomass derived high-octane fuel, wherein the trimerization of acetone in step (g) is carried out with a catalyst of manganese nitrate on silica gel.

In a thirty-third preferred embodiment there is provided in the twenty-first preferred embodiment a method of producing biomass derived high-octane fuel, wherein the trimerization of acetone in step (g) is carried out with a catalyst of manganese nitrate on a base of alumina washcoat on calcined aluminized stainless steel corrugated film.

In a thirty-fourth preferred embodiment there is provided in the first preferred embodiment a method of producing biomass derived high-octane fuel according, wherein the microorganism is clostridium or variants thereof.

In a thirty-fifth preferred embodiment there is provided in the sixteenth preferred embodiment a method of producing biomass derived high-octane fuel according, wherein the microorganism is clostridium or variants thereof.

DETAILED DESCRIPTION OF THE INVENTION

As discussed above, the present invention provides a non-petroleum-based renewable fuel comprised of fully renewable components, i.e., components derivable from bio-sources. In particular, as provided in the first embodiment herein, a bio-mass derived high-octane aviation fuel is provided, which is comprised of (a) at least one aromatic hydrocarbon, and (b) at least one isoparaffin having from 4 to 6 carbon atoms. This biomass-derived fuel has been experimentally demonstrated to have a high-octane rating, and is ideal for use in aviation applications. For example, the fuel of the present invention may be utilized as a replacement for the conventional 100 LL (low lead) aviation fuel used throughout the world in private aviation, as well as for use in turbine (jet) engine applications.

In a preferred embodiment, the aromatic hydrocarbon is sym-trimethyl benzene (mesitylene), also known as 1,3,5-trimethylbenzene. Various experimental studies were conducted to determine the effect of mesitylene concentration on MON, and in particular the optimal weight percent range thereof that provides the desired MON. The results of these tests, which applied the test standards under ASTM D2700 motor octane number in lean configurations, are shown in FIG. 1, wherein the X-axis denotes mesitylene concentration in weight percent, and the Y-axis denotes MON of the fuel.

Figure 1:
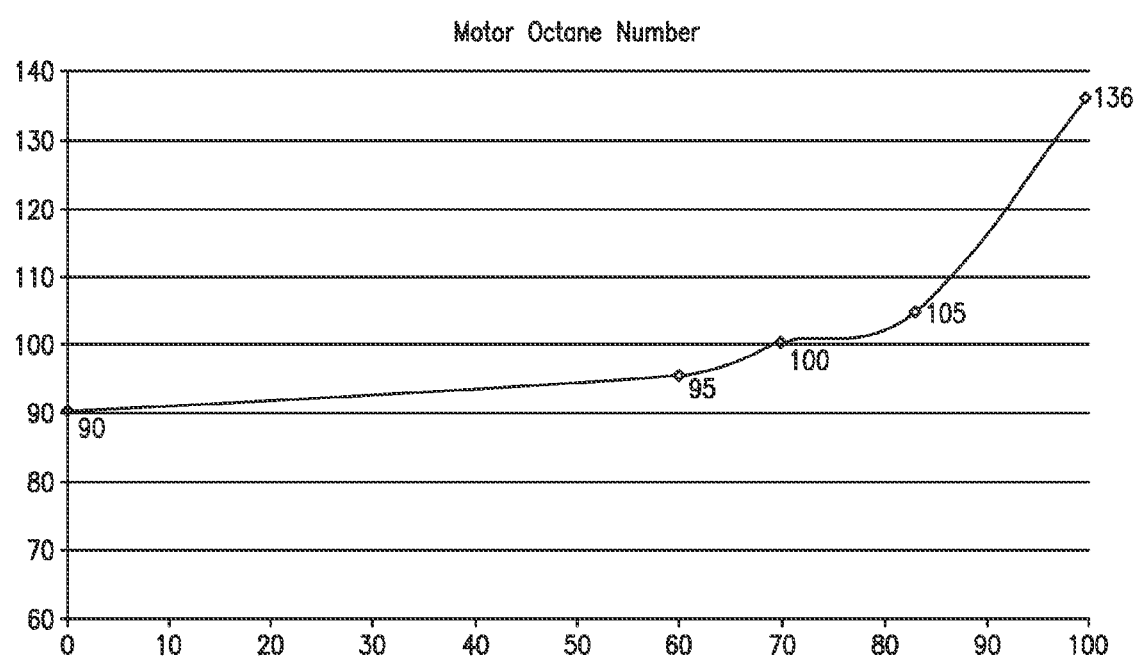
FIG. 1 is a graph of the motor octane number (MON) as a function of wt % of mesitylene for the biomass-derived high-octane fuel of the present invention.

Since the minimum motor octane number required for 100 LL octane aviation fuel is 99.5, it can be seen from FIG. 1 that all blends greater than about 70 wt % mesitylene meet that specification. In particular, when the aromatic hydrocarbon (mesitylene) is present in an amount of from about 60-85 wt %, a MON of from 96-105 is obtained. When the mesitylene constitutes 70-85 wt % of the fuel composition, the MON is observed to be 100 to 105. When the fuel contains mesitylene in an amount of 75 wt %, an MON of about 101-102 is obtained.

Figure 2:
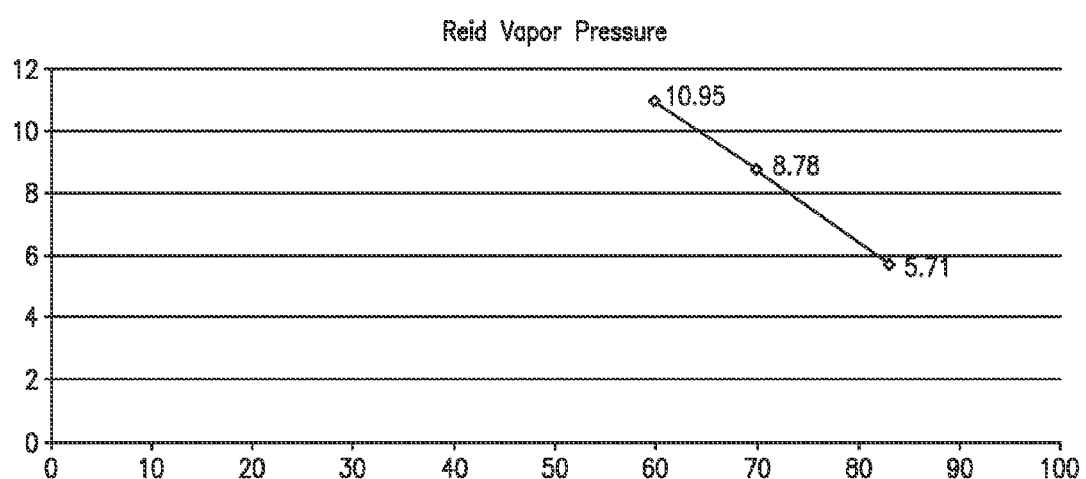
FIG. 2 is a graph of the Reid vapor pressure as a function of the wt % of mesitylene for the biomass-derived high-octane fuel of the present invention.
Figure 3A:
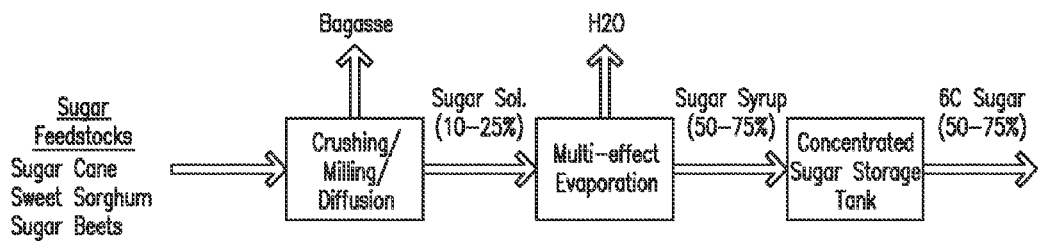
FIG. 3(a) is a process flow diagram illustrating the process of extracting 6C (six carbon-containing) sugars from sugar biomass feedstocks.
Figure 3B:
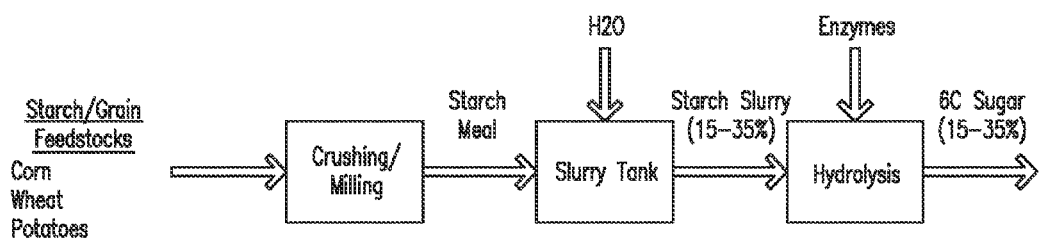
FIG. 3(b) is a process flow diagram illustrating the process of extracting 6C (six carbon-containing) sugars from starch/grain biomass feedstocks.
Figure 3C:
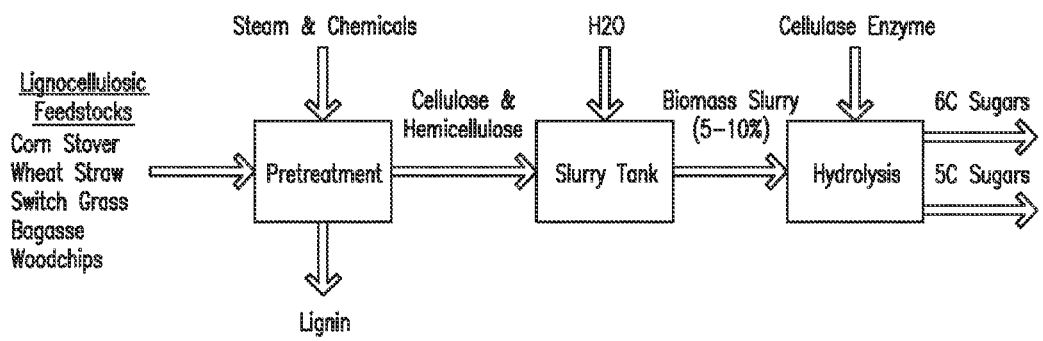
FIG. 3(c) is a process flow diagram illustrating the process of extracting 6C (six carbon-containing) sugars from ligno-cellulosic biomass feedstocks.
Figure 4A:
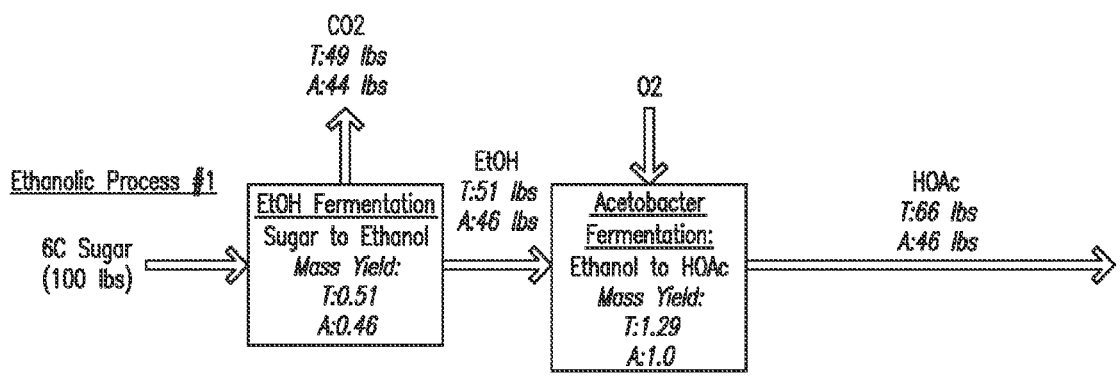
FIG. 4(a) is a process flow diagram illustrating an ethanolic process wherein 6C sugars are fermented first to ethanol, and then to acetic acid.
Figure 4B:
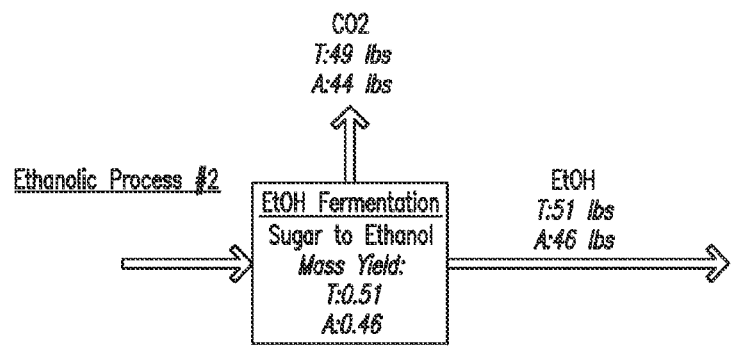
FIG. 4(b) is a process flow diagram illustrating an ethanolic process wherein 6C sugars are converted to ethanol.
Figure 4C:
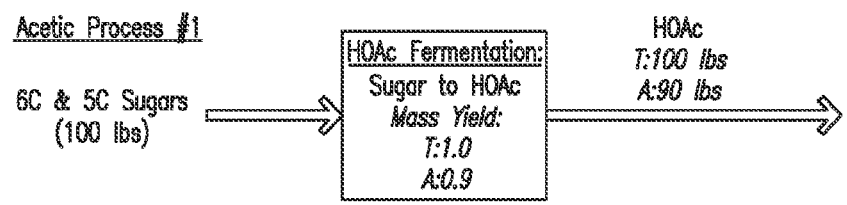
FIG. 4(c) is a process flow diagram illustrating an acetic process wherein 5C and 6C sugars are converted to acetic acid.
Figure 4D:
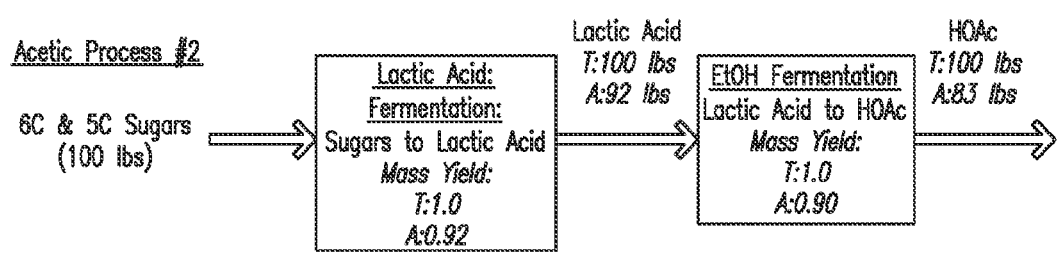
FIG. 4(d) is a process flow diagram illustrating an acetic process wherein 5C and 6C sugars are fermented to produce lactic acid, and lactic acid is then fermented to acetic acid.

Further tests were carried out according to ASTM D5191 to determine the Reid vapor pressure as a function of concentration (wt %) of mesitylene for the fuel of the present invention. The 0% and 100% (pure chemicals) were not tested. The results of these tests are illustrated in FIG. 2, wherein the X-axis denotes the concentration of mesitylene in weight percent, and the Y-axis denotes the Reid vapor pressure in psi (pounds per square inch). The Reid vapor pressure requirement of 100 LL octane aviation fuel is between 5.5 and 7.1 psi. As illustrated in FIG. 2, mesitylene concentrations of from about 70-85 wt % meet the Reid vapor pressure requirement for 100 LL octane aviation fuel. It should be noted that neither pure mesitylene nor pure isopentane meet this specification.

The isoparaffin of the above mentioned high-octane aviation fuel is present in the fuel in an amount of from about 15-40 wt %, more preferably 15-30 wt %. The isoparaffin is preferably a normally liquid isoparaffin, such as isopentane.

In an alternative embodiment of the present invention, a renewable fuel in accordance with the fuel of the first embodiment discussed above is provided, further comprising a straight chain alkane. Preferably, the straight chain alkane is a 3 carbon alkane, i.e., propane. Further, in this embodiment, rather than a branched chain 5 carbon alkane, such as isopentane as described above, a straight chain alkane, such as pentane is used. Such a fuel is preferably used as an automotive fuel.

In a further alternative embodiment of the present invention, a renewable fuel in accordance with the fuel of the first embodiment discussed above is provided, further comprising a straight chain alkane. Preferably, the straight chain alkane is a 3 carbon alkane, i.e., propane. Such a fuel is preferably used as a turbine engine fuel in aviation applications.

The present inventors conducted further tests according to six ASTM standards (methods) to determine various characteristics of pure mesitylene, pure isopentane, Swift 702 pure fuel according to the present invention (comprised of 83 wt % of mesitylene and 17 wt % isopentane) and conventional 100 LL aviation fuel. The results of these comparative tests are illustrated in Table 3 below:

Applicants unexpectedly discovered from these tests that adding isopentane to mesitylene in a certain concentration as called for herein increases the vapor pressure, lowers the freezing point, and lowers the 10% distillation point of mesitylene to within the ASTM standard as shown in Table 1. Applicants also unexpectedly discovered that adding mesitylene to isopentane to form a 100 octane aviation fuel raises the motor octane number of the isopentane (as compared to pure isopentane), raises the supercharge octane number of isopentane (as compared to pure isopentane), and lowers the vapor pressure of isopentane (as compared to pure isopentane) to within the ASTM D910 specification.

As mentioned above, the present inventors have further developed a method of producing bio-mass derived high-octane aviation fuel, comprising a first step of extracting 5C and 6C sugars from the biomass, and fermenting the extracted sugars with a microorganism or mutagen thereof to produce a mixture of metabolites comprising acetone and butanol. In particular, various processes may be utilized to ferment the sugars extracted from the biomass, as illustrated in FIGS. 3(a)-3(d). Then, as illustrated in FIGS. 4(a)-4(d), the sugars are fermented to produce ethanol or acetic acid. This fermentation step is preferably conducted in an anaerobic reactor in the absence of oxygen.

Various experimental tests were carried out to determine which microorganisms are most capable of converting the biomass-derived sugars to ethanol and acetic acid. The results of these tests, as well as the conditions under which these tests were carried out, are illustrated in Table 2 below.

TABLE 2

| Microorganism | Sugars Fermented | pH | Fermentation Temperature (° C.) | Fastest Doubling Time (Hours) | Acetate Produced (g/L) |
|---|---|---|---|---|---|
| Moorella Thermoaceticum | Glucose, Xylose | 7.2 | 57 | 6 | 25 |
| Thermoanaerobacter Kivui | Glucose | 6.5 | 66 | 3 | 43 |
| Moorella Thermoacetica | Glucose, Xylose, Lactic Acid | 7 | 55 | 10 | 20 |
| Moorella Thermoautotrophica | Glucose, Xylose, Lactic Acid | 6.5 | 60 | 10 | 30 |
| Moorella Thermoaeticum | Glucose, Xylose | 6.9 | 58 | 6 | 25 |
| Moorella Thermoautotrophicum | Glucose, Xylose | 6.9 | 56 | 6 | 35 |
| Thermoanaerobacter thermosaccharolyticum | Glucose | 6.9 | 45 | 6 | 20 |
| Morella Thermoaceticum | Glucose, Xylose | 6.9 | 60 | 6 | 90 |

TABLE 1

| ASTM Method | Test | Mesitylene | Isopentane | Swift 702 | 100 spec |
|---|---|---|---|---|---|
| D2700 | Motor Octane Number | 136 | 90.3 | 104.9 | ≥99.5 |
| D909 | Supercharge ON | 170 | 92.3 | 133.0 | 130.0 |
| D5191 | Vapor Pressure | ≤5.5 | ≥7.1 | 5.7 | 5.5 to 7.1 |
| D2386 | Freezing Pt | −49 | −161 | −63 | ≤58 |
| D86 | 10% Distillation Pt. | 165 | 28 | 65 | ≤75 |
| D86 | End Distillation Pt. | 185 | 28 | 165 | ≤170 |

In view of the results of the results of the tests discussed above, preferably, the microorganisms (MO's) used to carry out this fermentation process are one or more of moorella thermoaceticum, thermoanaerobacter kivui, moorella thermoacetica, moorella thermoautotrophica, moorella thermoaeticum, moorella thermoautotrophicum, thermoanaerobacter thermosaccharolyticum, moorella thermoaceticum. saccarophagus degradans strain 2-40, more preferably, thermoanaerobacter kivui, and/or moorella thermoaceticum are utilized, as they have been experimentally shown to produce the greatest acetone yield. However, selection of the MO's is dependent upon the particular biomass feedstock chosen, and can include, for example, clostridium and variants thereof.

The general classes of biomasses used as the base feedstocks in the method of production provided herein are those from which 5C and 6C sugars may be derived, such as sugars, celluloses, lignins, starches, and lignocelluloses. Preferably, hard woods, grasses, corn stover, sorghum, corn fiber, and/or oat hulls are utilized. To increase the efficiency of the fermentation process, preferably, these feedstocks are pretreated with enzymes or strong acids to break any hemicellulose chains into their sugar monomers.

Alternatively, in a preferred embodiment, ethanol may be produced from a plant material using the bioorganism saccharophagus degradans, strain 2-40. In particular, saccharophagus degradan is first grown in a first portion of the plant material. Then, protein is harvested from saccharophagus degradans, strain 2-40, and mixed with a second portion of the plant material and yeast in an aqueous mixture to produce ethanol.

The ethanol is then converted in whole or in part to acetone. Preferably, the ethanol is converted to acetone in the presence of iron oxide catalysts, or converted to acetone in the presence of zinc oxide-calcium oxide catalysts and water vapor. In addition, preferably, the acetone is separated from any remaining ethanol and/or other byproducts not converted to acetone in these processes.

In a second step of the method of the present invention, the acetone is separated from butanol, ethanol or other solvents in the metabolite mixture. In particular, the metabolites of acetone, butanol and ethanol produced in the first step are separated from the fermentation mixture when concentrations thereof exceed 2 to 3 wt %. It has been unexpectedly discovered that that this avoids possible poisoning of the microorganism or mutagens thereof. This may be performed using any conventional prior art process. In a preferable embodiment, fractional distillation is utilized to perform this function.

In a third step, a portion of the resultant acetone produced in the second step is dimerized to form isopentane. Any conventional process may be utilized to carry out this dimerization step. Preferably, however, dimerization of acetone is carried out in a catalytic reaction to yield isopentane. Most preferably, this dimerization step is carried out in a gas phase catalytic reaction.

In a fourth step, another portion of the acetone derived in the second step described above is trimerized to form mesitylene. As in the third step above, the trimerization process may be carried out using any conventional trimerization process. Preferably, the trimerization of acetone is carried out in the gas phase by reacting acetone with sulfuric or phosphoric acid at elevated temperatures. Further, this trimerization step is preferably carried out in the presence of a catalyst.

In order to tailor the catalyst for the three control parameters above, the surface acidity is preferably controlled. Changing to a more acidic substrate such as silica gel or amorphous silica or a more neutral catalyst substrate such as alumina have shown unexpected results due to surface acidity.

The trimerization catalyst preferably contains at least one metal selected from the group consisting of Row 4 transition metals (V, Cr, Mn, Fe, Co, Ni, Cu), Row 5 transition metals (Nb, Mo, Ag), and Row 6 transition metals (W), all as fully developed oxides.

Preferably, Column 2A alkaline earth metals (Mg, Ca, Sr, Ba), and Column 1A alkaline metals (Na, K) as the developed oxides, are effective as promoters or co-catalysts in the trimerization catalysts.

The catalyst of the present invention is preferably comprised of three portions, (1) a catalyst substrate or base with a defined surface acidity and surface area, (2) the catalyst itself which is preferably dispersed on the substrate as a developed oxide and, optionally, (3) a promoter or co-catalyst which is preferably an alkaline species which tailors the overall acid properties of the catalyst ensemble.

In order to tailor the catalyst for the three controlled parameters above, the surface acidity is preferably controlled. Changing to a more acidic catalyst substrate such as silica gel or amorphous silica or a more neutral catalyst substrate such as alumina have produced unexpected results due to surface acidity.

In low flow systems, it is preferred to use a catalyst in bead form. These catalysts are prepared by using a base of alumina or silica catalyst base, in bead form, which can be soaked with a defined volume of impregnating solution. The volume of impregnating solution is defined by the apparent bulk density (ABD) of the catalyst base. The concentration of the impregnating solution can be adjusted such that a defined amount of solution is in contact with the catalyst base. For example, 107.05 g of alumina beads are contacted with 27.83 g of ferric nitrate nonahydrate dissolved to make 100 ml of impregnating solution. The alumina beads have an ABD of 0.7146, hence the dry volume is 150 ml. The 100 ml of impregnating solution just covers the particular catalyst base. The base and the solution are left in contact for one hour. The mix is dried in a drying oven at 200° C. until at constant weight. The dried catalyst is calcined in a calcining furnace overnight at 700° C. In this example, 3.58 g of stable iron oxide is deposited on 150 ml of base, which is more conveniently expressed as 675 g per cubic foot.

In high flow rate systems, monolithic catalysts is preferably used. In the monolithic catalyst, a defined slurry of catalyst compound is placed in contact with a continuous ribbon of a metallic substrate bonded to an alumina wash coat. The slurry is dried, then calcined similar to the process above. The slurry concentration and temperatures for drying and calcining are chosen to ensure the correct deposition and fixation of the defined oxide. The deposited catalyst is expressed in units of grams per cubic foot similar to the method discussed above. Preferred high flow rate catalysts include manganese nitrate and niobium oxide.

Figure 5:
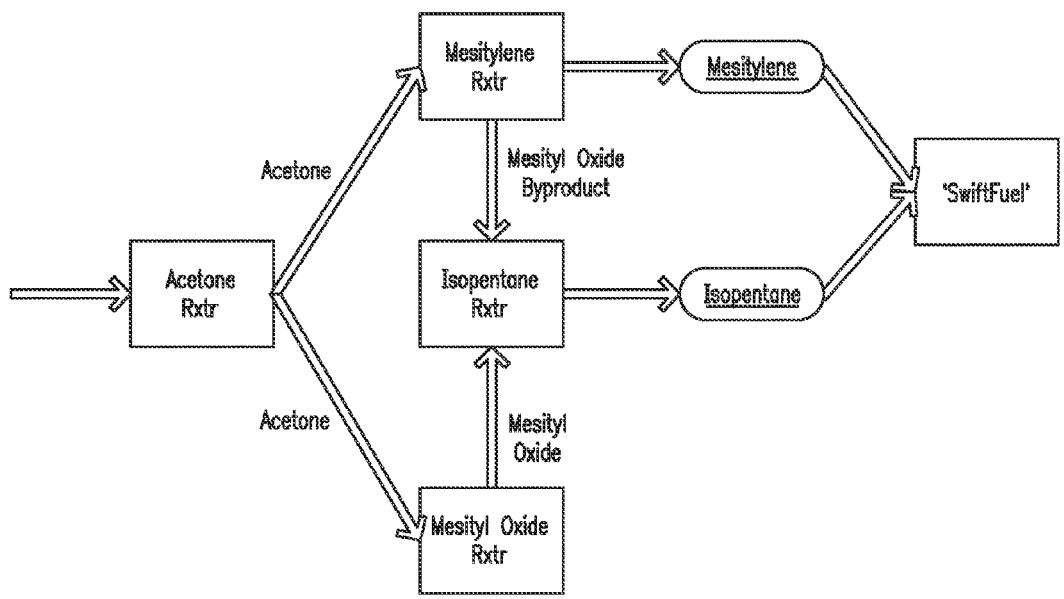
FIG. 5 is a process flow diagram illustrating the process wherein the acetic acid produced in the processes shown in FIGS. 4(a), 4(c) and 4(d) is converted to acetone, the acetone is then converted to mesitylene and isopentane, and finally combined to produce the fuel of the present invention.
Figure 6:
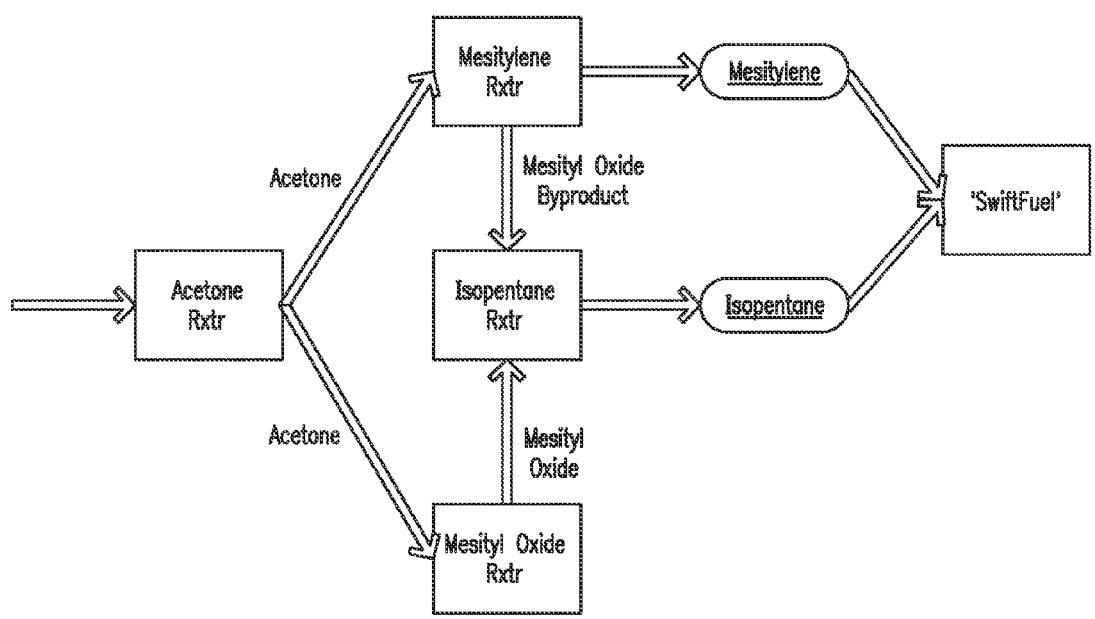
FIG. 6 is a process flow diagram illustrating the process wherein the ethanol produced in the process shown in FIG. 4(b) is converted to acetone, the acetone is then converted to mesitylene and isopentane, and finally combined to produce the fuel of the present invention.

Lastly, the mesitylene with the isopentane derived in the third and fourth steps described above are mixed in the appropriate proportions to form synthetic high-octane aviation fuel. Specifically, the proportions of these components are mixed in the weight percentages described above. The process steps utilized to carry out the third through fifth steps of the present invention are illustrated in FIGS. 5 and 6.

Figure 7:
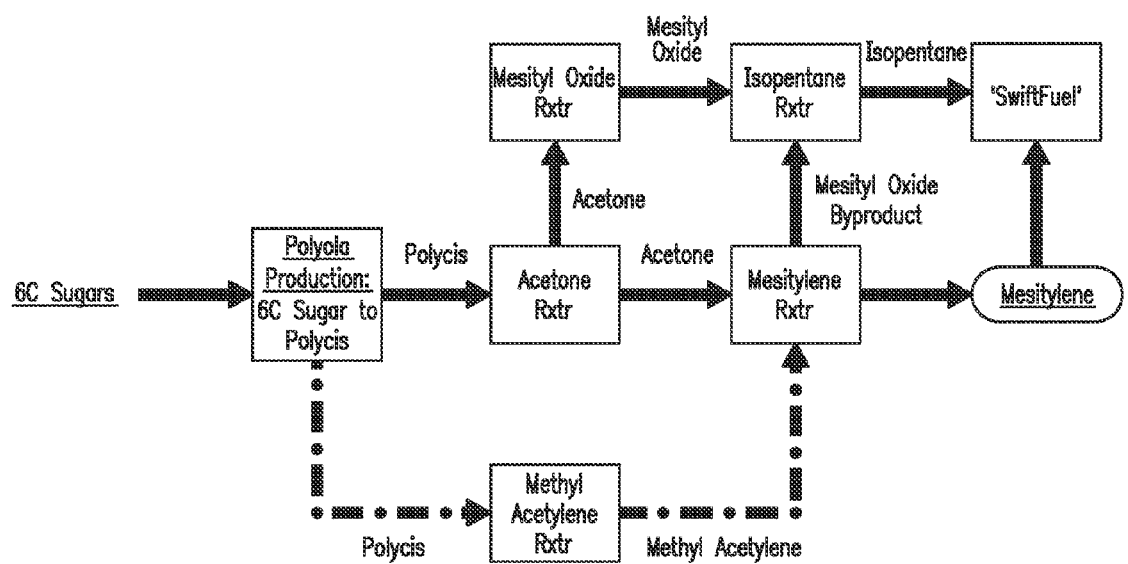
FIG. 7 is a process flow diagram illustrating a process of converting 6C sugars to the fuel of the present invention.

An alternative overall process view is illustrated in FIG. 7. In this alternative embodiment of the present invention, natural gas or gas produced from biomass is converted to propane, propane is converted to propyne (methylacetylene), and propyne to mesitylene and isopentane. It should be noted that this reaction process is similar to the method of manufacture discussed above using acetone. However, no water is generated, and the reaction is all gas phase.

It should be recognized that the alternative embodiment fuels mentioned above comprising, for example, pentane or propane, are manufactured using the above described process. However, the pentane and propane components can be derived from acetone instead of, or in addition to, the mesitylene and isopentane components in a similar manner. Further, if desired, conventional fuel additives, such as surfactants, viscosity improvers, anti-icing additives, thermal stability improver additives, and metal de-activators to suppress the catalytic effect which some metals, particularly copper, have on fuel oxidation. However, these additional components must be selected with care so as to ensure that they have no effect on the MON, Reid vapor pressure, etc.

In another preferred embodiment mesitylene can be made in a process including (1) fermentation of a biomass to form ethanol, (2) a dehydration reaction of ethanol to form acetone and water, (3) the separation by distillation of unreacted ethanol from water and acetone, and (4) the gas phase reaction of acetone to form mesitylene. For the reaction step ethanol can be metered out and then vaporized. The ethanol vapor can be superheated to 350° C. at 100 psig and then the superheated vapor is passed through a reactor containing a catalyst bed. A preferred catalyst is zinc oxide/calcium oxide, for the ethanol to acetone reaction.

After being decompressed to atmospheric pressure, the gas is liquefied in a condenser and collected. Preferably, a dry ice condenser liquefies any vapors that pass through a primary condenser that are condensable down to minus 78° C. The raw product can then be distilled, unreacted ethanol (overheads) being separated from acetone and water (bottoms), and through a gas phase reaction to form mesitylene from the acetone. The ethanol (overhead stream) can be recycled to the reactor.

As long as there is no acetone present, water can be separated from mesitylene via a phase separator because of their mutual low solubility. The water (heavy phase) can then be drawn off and disposed of. Mesitylene can be sampled and stored. The condensed ethanol can be recycled back to the reactor feed tank. The condensed acetone can be recycled as well.

Although specific embodiments of the present invention have been disclosed herein, those having ordinary skill in the art will understand that changes can be made to the specific embodiments without departing from the spirit and scope of the invention. The scope of the invention is not to be restricted, therefore, to the specific embodiments. Furthermore, it is intended that the appended claims cover any and all such applications, modifications, and embodiments within the scope of the present invention.

In a seventeenth embodiment of the present invention, the present inventors discovered a synthetic high octane aviation fuel comprising:
(a) at least one aromatic hydrocarbon, and
(b) at least one isoparaffin having from 4 to 6 carbon atoms.

In an eighteenth embodiment of the present invention, the present inventors discovered the synthetic high octane aviation fuel of the seventeenth embodiment, wherein the aromatic hydrocarbon is present in an amount of at least about 60 wt %; and the isoparaffin is present in an amount of at least about 15 wt %.

In a nineteenth embodiment of the present invention, the present inventors discovered the high synthetic octane aviation fuel of the seventeenth embodiment, wherein the aromatic hydrocarbon is present in an amount of no more than about 85 wt %; and the isoparaffin is present in an amount of no more than about 40 wt %.

In a twentieth embodiment of the present invention, the present inventors discovered the synthetic high octane aviation fuel of the seventeenth embodiment, wherein the aromatic hydrocarbon is sym-trimethyl benzene (mesitylene).

In a twenty-fourth embodiment of the present invention, the present inventors discovered the synthetic high octane aviation fuel of the twentieth embodiment, wherein the mesitylene is present in an amount of at least about 70 wt %.

In a twenty-fifth embodiment of the present invention, the present inventors discovered the synthetic high octane aviation fuel of the twentieth embodiment, wherein the mesitylene is present in an amount of between about 70 to 85 wt %.

As discussed above, the present invention provides a non-petroleum-based renewable fuel comprised of fully renewable components, i.e., components derived from biosources. In particular, as provided in the first embodiment herein, a renewable fuel is provided comprised of (a) one or more low carbon esters derivable from ethanol, (b) one or more pentosan derivable furans, (c) one or more aromatic hydrocarbons derived from acetone or propyne, (d) one or more $C_6$-$C_8$ straight chain alkanes derivable from polysaccharides and (e) one or more bio-oils derived from plant germ. In addition, as provided in the fourteenth and fifteenth embodiment herein, the renewable fuel may contain triethanolamine, which provides lubricity. Amines have been known to increase lubricity in internal combustion engines; triethanolamine having such a property when used with the other renewable components.

With regards to component (a), i.e., low carbon number esters, it is preferable to utilize esters having a carbon number of 1-4, such as ethyl acetate, butyl acetate or propyl acetate. Most preferably, ethyl acetate is used, as ethyl acetate provides an increase in the fuel's vapor pressure, essential for cold weather operations. These low carbon number esters are derivable from ethanol, using processes such as direct reaction with acetic acid in the presence of sulfuric acid. Further, the acetic acid can be directly derived from ethanol, if desired. All of these components can be derived from kernel corn, switchgrass or other cellulosic or sugar based materials.

With regards to component (b), i.e., pentosan derivable furans, it is preferable to utilize substituted furans. Most preferably, 2-methyl furans are used. The pentosan derivable furans are derived from corn stalks, stalks of other grains, and potentially, grasses. Specific furans are used as octane and energy increasing components.

With regards to component (c), i.e., aromatic hydrocarbons, unlike conventional petroleum-based fuels, the present invention comprises aromatic hydrocarbons derived from acetone, a fully renewable source. Most preferably, the aromatic hydrocarbon is mesitylene. Mesitylene can conveniently be prepared by the trimerization of acetone or propyne; acetone can be readily prepared from biomass, and propyne can be extracted from natural gas. Mesitylene is preferred, since the acetone or propyne reaction "stops" at the trimer, which makes the conversion high due to lack of significant side-reactions. Mesitylene can be used as an octane and energy enhancing ingredient.

With regards to component (d), i.e., straight chain alkanes in the $C_4$ to $C_{10}$ range, the alkanes are derived from biomass, specifically polysaccharides derived from biomass. Straight chain alkanes have the lowest octane number of a given set of alkane isomers; the more branched the molecule, the smoother combusting (higher octane) the molecule exhibits when tested. Preferably $C_5$ to $C_9$ straight chain alkanes are utilized. Most preferably $C_6$ to $C_8$ straight chain alkanes are included in the fuel. These straight chain alkanes act as octane depressants within the fuel. Most preferably, the straight chain alkanes are one or more chosen from n-pentane, n-hexane, n-heptane, n-octane, and n-nonane.

Lower straight chain alkanes, such as n-pentane, n-butane, propane and below, have too low of a boiling point to be useful as a main component of the developed fuel. Higher straight chain alkanes, such as n-nonane, n-decane and above, have too high of a carbon-to-hydrogen molecule fraction (>0.444). This high fraction leads to incomplete combustion in heat engines and coking. Straight chain alkanes are used to suppress the octane of a given fuel, while maintaining a high energy content per unit volume. Higher alkanes can be used in diesel and jet turbine applications.

With regards to component (e), i.e., bio-oils derived from plant germ, these components may be derived from various plant sources. For example, the bio-oil may include soybean oil, rapeseed oil, canola oil or corn oil, palm oil, and combinations thereof. Most preferably, corn oil is utilized as the bio-oil component because of its enhancement of energy, fuel's physical properties, and lubricity properties. Corn oil is derived directly from the corn germ.

Further, optionally, as called for in the fourteenth embodiments herein, the renewable fuel of the present invention may additionally contain component (f), i.e., triethanolamine. The inclusion of triethanolamine in the renewable fuel provides the advantage of lubricity at low concentrations, as well as effective octane improvement due to the combustion inhibition properties of the nitrogen moiety. Triethanolamine can be derived from ammonia and ethylene, both of which can be conveniently produced from biomass.

It was unexpectedly discovered by the present inventors that, by combining the above components (a)-(f) in the weight ranges called for herein in the second and fifteenth embodiments herein, a completely non-petroleum-based fuel, fully derivable from renewable biomass sources, could be obtained. Further, it was discovered that the fuel components could be conveniently adjusted to produce an appropriate air to fuel ratio for application in a heat engine. In the case of aircraft engines, that value was 14.2 to 1, based on mass. Further, it was unexpectedly discovered that this renewable fuel can be formulated to have a very high octane, e.g., up to 160 MON, by varying the octane increasing ingredients, such as the furans, with the energy increasing components such as mesitylene and corn oil.

Alternatively, as called for in the present invention, the present inventors unexpectedly discovered that the renewable fuel of the present invention can be formulated to have a much lower octane rating, such as 84 MON, which can be, for example, utilized as an automotive fuel. In particular, a high energy, octane depressant (component (d)), such as n-heptane, can be added to the fuel to obtain a lower octane rated fuel for use in conventional automotive and aviation applications. Another method of formulating a lower octane fuel, known as "derating", includes the substitution of acetone or tetrahydrofuran or other low octane ingredients for the ethyl acetate, while increasing the energy content.

Representative examples of the renewable fuels (identified in the column labeled "Invention Formulation") of the present invention, which have been prepared in the laboratory, are shown below in Table 1.

TABLE 1

"Composition Matrix for Invented Formulations"

| Formulation | Ethyl Acetate | 2-Methyl Furan | Mesitylene | n-Heptane | Corn Oil |
|---|---|---|---|---|---|
| High Octane AvGas | 17.5% | 17.5% | 60.0% | 0.0% | 5.0% |
| 100LL Replacement | 13.1% | 13.1% | 45.0% | 25.0% | 3.8% |
| Auto Gas | 9.0% | 10.0% | 36.0% | 40.0% | 5.0% |

TABLE 1-continued

"Composition Matrix for Invented Formulations"

| Formulation | Ethyl Acetate | 2-Methyl Furan | Mesitylene | n-Heptane | Corn Oil |
|---|---|---|---|---|---|
| Turbine Fuel | 8.0% | 24.0% | 60.0% | 0.0% | 8.0% |
| Turbine Fuel 2 | 0.0% | 0.0% | 0.0% | 63.0% | 37.0% |
| Diesel Fuel | 0.0% | 0.0% | 0.0% | 63.0% | 37.0% |
| Rocket Fuel | 0.0% | 0.0% | 60.0% | 35.0% | 5.0% |

PREPARATION EXAMPLE:

4-cycle engine fuel 17.5 grams of ethyl acetate were mixed with 17.5 grams of 2-methyl furan. 60 grams of mesitylene were then added, followed by 5 grams of corn oil, to form 100 grams of fuel of the present invention. The mixture was stirred until all components were dissolved. The resulting solution was then analyzed, and found to have an effective MON of 142, and an optimum mixture ratio of 14.2 based on mass. This fuel has been effectively demonstrated in low and high compression reciprocating aviation engines.

Test Examples

In order to determine the characteristics of the renewable engine fuel of the present invention (representative examples of which are described as "Invention Formulation" in Table 1 above), the present inventors prepared the following fuels of the present invention (denoted in Table 2 as "100 LL Replacement" and "High Octane AvGas"), and conducted calorimetric tests thereof. In particular, calorimetry was conducted in a Parr combustion bomb. Octane measurements were done by variable compression ratio engine testing under more severe conditions to assess Motor Octane Number (MON).

Bulk calorimetry accurately determines the energy content (heat of combustion) of a given component or mixture. MON values were conducted by Intertek Caleb Brett® under the ASTM D2700M methodology.

Through thermophysical analysis and initial formulation, a series of four- and five-part mixtures according to the present invention, as shown in Table 2 below, were prepared, which have been shown through testing to be capable of directly replacing conventional 100 LL Aviation Fuel and conventional High Octane Aviation Fuel. The composition information for these fuels is found in Table 1.

Upon further testing in the laboratory, through the use of a bulk calorimeter, the present inventors have confirmed that the test results for the renewable fuel of the present invention (denoted as 100 LL Replacement in Tables 1 and 2) are comparable with the currently used 100 LL aviation fuel properties. The characteristics of these renewable fuels of the present invention, obtained through testing as described above, are shown in Table 2. Also shown in Table 2 are the physical and chemical properties for conventional 100 LL aviation fuel, for comparison, shown as the second column under "Current Fuel".

TABLE 2

"Comparison of Current 100LL Aviation Fuel and Invented Aviation Fuels"

| Characteristic | Units | Current Fuel | 100LL Replacement | High Octane AvGas |
|---|---|---|---|---|
| Motor Octane Number | | ≥101 | 107 | 142 |

TABLE 2-continued

"Comparison of Current 100LL Aviation Fuel and Invented Aviation Fuels"

| Characteristic | Units | Current Fuel | 100LL Replacement | High Octane AvGas |
|---|---|---|---|---|
| Net Heat of Combustion | kcal/cc | ≥7.49 | 7.96 | 7.99 |
| Air to Fuel Ratio | w/w | ≥14.00 | 15.13 | 14.20 |
| Average Empirical Formula | | $C_8H_{18}$ | $C_{9.1}H_{15}O_{0.7}$ | $C_{9.8}H_{14}O$ |
| Flame Temperature | °K. | ≥1906 | 2130 | 2140 |
| Density at 15° C. | kg/m³ | ≥720.3 | 831.4 | 882.1 |
| Tetraethyl lead | gPb/l | 0.56 | 0 | 0 |
| Sulphur | % mass | ≤0.05 | 0 | 0 |
| Initial Boiling Point | ° C. | | 65 | 65 |
| Freezing Point | ° C. | ≤−58 | −66 | −58 |
| Final Boiling Point | ° C. | ≤168 | 165 | 165 |
| Hodges Vapor Pressure | kPa | 37 to 87 | 58 | 60 |
| Visible Lead Precipitate | mg/100 ml | ≤3 | 0 | 0 |
| Flame Color | | Orange | Orange | Orange |

The ethanol-based renewable fuels of the present invention can be derived from biosources, hence they are truly renewable. Furthermore, two of the components are directly synthesized from ethanol; which makes this technology complementary to existing and future ethanol plants. The raw materials for each of the components are polysaccharides or germ oils in some form; these have current and projected market prices.

What is claimed is:

1. A method of producing bio-mass derived high-octane fuel, comprising the steps of:
   (a) fermenting a biomass with a microorganism or a mutagen thereof to produce a mixture of metabolites comprising acetone and butanol;
   (b) separating the acetone from butanol and any ethanol or other solvents in the mixture by fractional distillation;
   (c) dimerizing a portion of resultant acetone from step (b) to form isopentane;
   (d) trimerizing another portion of the acetone from step (b) using a catalyst containing at least one metal selected from the group consisting of niobium, iron, and manganese to form mesitylene, and
   (e) mixing the mesitylene with the isopentane from steps (c) and (d), whereby to form the biomass-derived high-octane fuel.

2. The method of producing bio-mass derived high-octane fuel of claim 1, wherein the microorganisms are one or more chosen from among thermoanaerobacter kivui, moorella thermoacetica, moorella thermoautotrophica, thermoanaerobacter thermosaccharolyticum, and saccharophagus degradans, strain 2-40.

3. The method of producing bio-mass derived high-octane fuel of claim 1, wherein the biomass is selected from the group consisting of sugars, celluloses, lignins, starches, and lignocelluloses.

4. The method of producing bio-mass derived high-octane fuel of claim 1, wherein the biomass is selected from the group consisting of hard woods, grasses, corn stover, sorghum, corn fiber, and oat hulls, which are pretreated with enzymes or strong acids to break any hemicellulose chains into their sugar monomers.

5. The method of producing bio-mass derived high-octane fuel according to claim 1, wherein the fermentation in step (a) is conducted in an anaerobic reactor in the absence of oxygen.

6. The method of producing bio-mass derived high-octane fuel of claim 1, wherein metabolites of acetone, butanol and any ethanol from step (a) are stripped from the fermentation when concentrations thereof over 2 to 3 wt % are obtained, whereby to avoid any poisoning of the microorganism.

7. The method of producing bio-mass derived high-octane fuel of claim 1, wherein the trimerizing of acetone in step (d) is carried out in the gas phase by passing acetone in contact with a catalyst containing niobium oxide at elevated temperatures.

8. The method of producing bio-mass derived high-octane fuel of claim 1, wherein the dimerization of acetone in step (c) is carried out in a catalytic reaction to yield isopentane.

9. The method of producing bio-mass derived high-octane fuel of claim 1, wherein the dimerization of acetone in step (c) is carried out in a gas phase catalytic reaction.

10. The method of producing bio-mass derived high-octane fuel of claim 7, wherein the trimerization of acetone in step (d) is carried out with a catalyst of niobium oxide on a base of alumina washcoat on calcined aluminized stainless steel corrugated film.

11. The method of producing biomass derived high-octane fuel of claim 7, wherein the trimerization of acetone in step (d) is carried out with a catalyst of niobium oxide on a base of alumina beads.

12. The method of producing biomass derived high-octane fuel of claim 7, wherein the trimerization of acetone in step (d) is carried out with a catalyst of niobium oxide on silica gel.

13. The method of producing biomass derived high-octane fuel of claim 7, wherein the trimerization of acetone in step (d) is carried out with a catalyst of manganese nitrate on alumina beads.

14. The method of producing biomass derived high-octane fuel of claim 7, wherein the trimerization of acetone in step (d) is carried out with a catalyst of manganese nitrate on silica gel.

15. The method of producing biomass derived high-octane fuel of claim 7, wherein the trimerization of acetone in step (d) is carried out with a catalyst of manganese nitrate on a base of alumina washcoat on calcined aluminized stainless steel corrugated film.

16. The method of producing biomass derived high-octane fuel according to claim 1, wherein the microorganism is clostridium or variants thereof.

* * * * *